US008115135B2

(12) United States Patent
Kuo

(10) Patent No.: US 8,115,135 B2
(45) Date of Patent: Feb. 14, 2012

(54) PLASMA ASSISTED OXYGEN DECONTAMINANT GENERATOR AND SPRAYER

(75) Inventor: Spencer P Kuo, River Edge, NJ (US)

(73) Assignee: Adventix Technologies Inc., River Edge, NJ (US)

( * ) Notice: Subject to any disclaimer, the term of this patent is extended or adjusted under 35 U.S.C. 154(b) by 1036 days.

(21) Appl. No.: 12/030,962

(22) Filed: Feb. 14, 2008

(65) Prior Publication Data

US 2008/0173621 A1    Jul. 24, 2008

(51) Int. Cl.
B23K 10/00    (2006.01)
(52) U.S. Cl. .......... 219/121.48; 219/121.52; 219/121.59
(58) Field of Classification Search ............. 219/121.36, 219/121.48, 121.54, 121.5, 121.51, 74, 75, 219/121.52
See application file for complete search history.

(56) References Cited

U.S. PATENT DOCUMENTS

| 6,329,628 B1* | 12/2001 | Kuo et al. | 219/121.54 |
| 7,091,441 B1* | 8/2006 | Kuo | 219/121.36 |
| 7,592,564 B2* | 9/2009 | Kumar et al. | 219/121.43 |
| 7,777,151 B2* | 8/2010 | Kuo | 219/121.47 |

* cited by examiner

Primary Examiner — Mark Paschall

(57) ABSTRACT

An atomic oxygen generator/sprayer is invented. An array of three magnetized torches running at 60 Hz is used to generate non-thermal plasma; thus, the plasma effluent has relatively low temperature (touchable) and yet contains high energy electrons (>5 eV) capable to dissociate oxygen molecules to atomic oxygen. The emission spectroscopy of the torch indicates that the plasma effluent carries an abundance of reactive atomic oxygen (RAO), which can effectively kill all kind microbes. A cap holding three pairs of rectangular permanent magnets is used to spread torches laterally into fan shape, which extends to a width exceeding 100 mm. The flux of RAO exceeds $2 \times 10^6$ cm$^{-2}$ sec$^{-1}$; its flow speed exceeds 20 m/s and it reaches out more than 20 mm. This invention is suitable for applications such as sterilizing carpets, clothes, and bed sheets.

6 Claims, 8 Drawing Sheets ns to spread the generated torches to a fan-shape and also separating the hot regions of the torches from the application region. It is found that the plasma effluent carries abundant RAO, which can effectively kill all kind microbes. The RAO flux can reach carpet underlay, where cannot be sterilized easily by the conventional methods. A photo of an assembled product is presented in FIG. 2.

ROS are inferred by the emission spectroscopy of the plasma effluent. The emission profile at 777.4 nm shown in FIG. 3 is a clear evidence of atomic oxygen generated by the torch. The produced RAO spreads laterally by the magnets and reaches out more than 20 mm. The operation of the invention is demonstrated in FIG. 4.

PLASMA ASSISTED OXYGEN DECONTAMINANT GENERATOR AND SPRAYER

§1. BACKGROUND OF THE INVENTION

§1.1 Field of the Invention

The present invention generally concerns the design of an array of air plasma torches, which are spread into fan-shape to have larger exposure width. The plasma effluent produced by the device carries abundant atomic oxygen, which can effectively kill all kind microbes. Applications of the device include sterilization of carpets, clothes, and bed sheets, a dry approach and no chemical materials used.

§1.2 Background

Described in the article "Design and electrical characteristics of a modular plasma torch," IEEE Trans. Plasma Sci., Vol. 27, no. 3, pp. 752-758, 1999; and in the U.S. Pat. No. 6,329,628 titled "Methods and Apparatus for Generating a Plasma Torch," ("the '628 patent") by S. P. Kuo, et al., an array of arc torches can be run simultaneously in low frequency (e.g., 60 Hz) periodic mode by a single power supply. In an array arrangement, the covered area of produced plasma can be enlarged considerably. A device employing an array of torches to generate plasma for the application of carpet sterilization is devised. The device spreads each torch, normally having a cylindrical shape, in the array to a fan-shape, so that the plasma effluent produced by the torch array covers an extended wide region. Moreover, this device produces low temperature non-equilibrium air plasma carrying abundant atomic oxygen, which can effectively kill all kind microorganisms including the toughest biological agents, bacterial spores, such as Anthrax (See, e.g., the articles: H. W. Herrmann et al., "Decontamination of chemical and biological warfare (CBW) agents using an atmospheric pressure plasma jet (APPJ)," Phys. Plasma, Vol. 6, pp. 2284-2289, 1999 (hereafter referred to as "the Herrmann article"); and Wilson Lai et al., "Decontamination of Biological Warfare Agents by a Microwave Plasma Torch", Phys. Plasmas, Vol. 12, 023501 (1-6), February 2005 (hereafter referred to as "the Lai article")). The plasma effluent has a large flow speed (>20 m/s) to penetrate through the carpet. Thus, this sterilizer kills microbes in the carpet as well as those accumulated behind the carpet.

The advantages of producing non-equilibrium plasma are 1) the plasma effluent is low temperature and thus does not burn the carpet and 2) having a better usage of the electron plasma energy, gained from the discharge, for the production of reactive oxygen species (ROS), rather than for heating the torch. ROS (particularly, the reactive atomic oxygen (RAO)) are the decontaminant.

§2. SUMMARY OF THE INVENTION

Vacuum cleaner removes dust from carpets and stains on carpets can be removed by a steamer/shampoo machine. However, those machines do not disinfect carpets, which usually accumulate all kind microbes, in particular, in the carpet underlay.

A carpet sterilizer is devised. A drawing of the system is presented in FIG. 1. The right-hand side container contains a power supply and an air pump. On the left, it is a device producing a fan-shaped torch for sterilization. This device uses an array of three torch modules to generate air plasma and a rectangular cap hosting three pairs of permanent magnets to spread the generated torches to a fan-shape and also separating the hot regions of the torches from the application

§3. BRIEF DESCRIPTION OF THE DRAWINGS

§4. DETAILED DESCRIPTION

The present invention involves a novel design of a plasma spray device, which uses an array of three torch modules for plasma generation and three pairs of rectangular permanent magnets to spread torches laterally. The working gas is air and this device produces abundant reactive atomic oxygen (RAO) in the plasma effluent, which is dry decontaminant and penetrates easily into carpet to kill microbes. The following description is presented to enable one skilled in the art to make and use the invention, and is provided in the context of a particular application and its requirement. Various modifications to the disclosed embodiments will be apparent to those skilled in the art, and the general principles set forth below may be applied to other embodiments and applications. Thus, the present invention is not intended to be limited to the embodiments shown.

In the following, functions, which may be performed by the present invention, are introduced in §4.1. Then, structures of the apparatus built in accordance with the present invention are described in §4.2. Application of the invention is described in §4.3. Thereafter, operations of the apparatus are described in §4.4. Finally, conclusions about the present invention are presented in §4.5.

§4.1 Functions

The present invention may be used to generate and spread atomic oxygen (OI) as dry decontaminant to kill microorganisms. The plasma torches carrying abundant OI are produced by an array of three torch modules and spread to a fan-shape to cover a wide area (e.g., about 100×10 mm) in open region. A considerable flux of reactive atomic oxygen is produced and reaches out more than 20 mm. RAO can effectively kill all kind microbes. The plasma effluent flowing out the cap does not burn carpets; the present invention does not rely on the heat produced by the torch for the sterilization. In other words, it is safe to have a close contact of this dry decontaminant with the objects (e.g., carpets, bed sheets, and paper).

§4.2 Structures

In the following, a torch device that may be used for sterilizing carpets is described.

Figure 1:
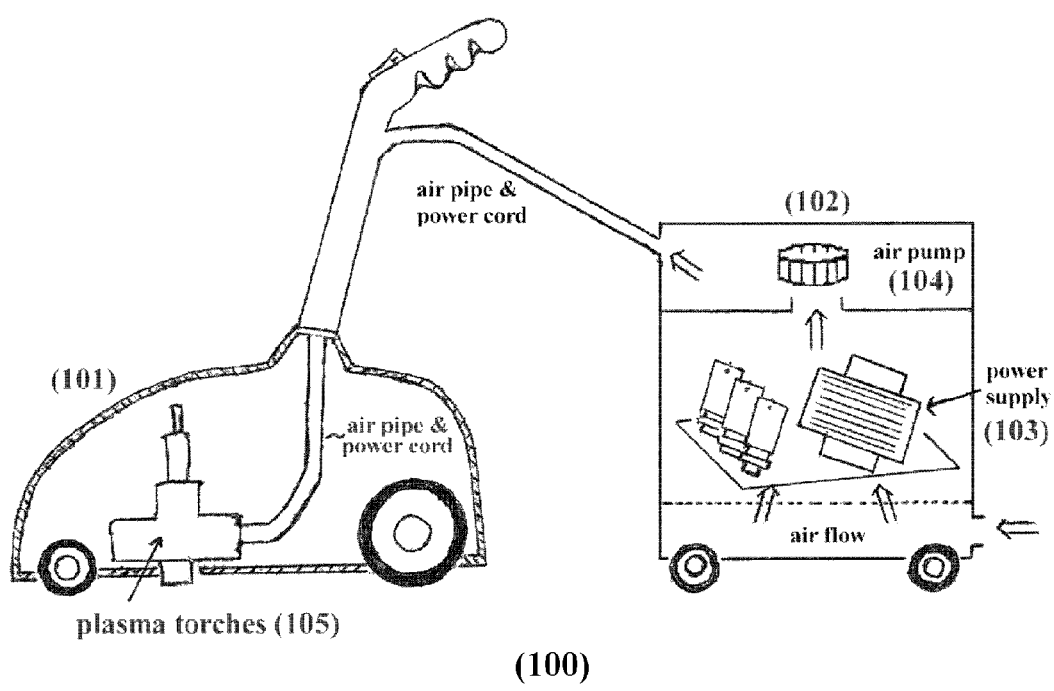
FIG. 1 is a drawing of the carpet cleaning device.

This device as layout in FIG. 1 consists of two parts (101, 102) which are connected by an air duct and a power cord. On the left (101) in FIG. 1, it is a device producing a fan-shaped torch for sterilization. In the container (102) shown on the right hand side of FIG. 1, there are a power supply (103) and an air pump (104). Air sucked into the container is first used to cool the power supply and then blown by the air pump to the plasma torches (105) through the connected duct.

Figure 5:
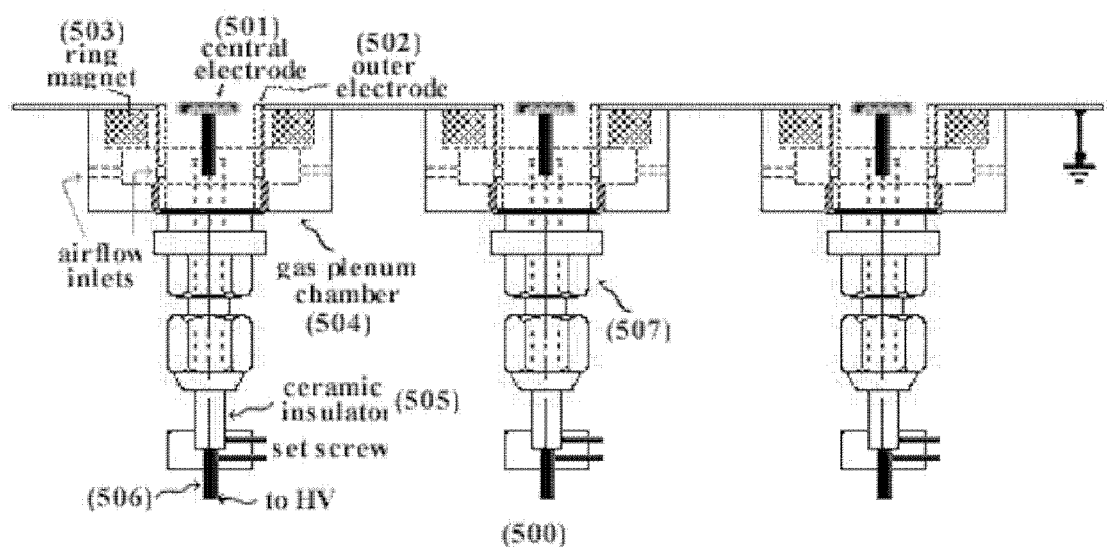
FIG. 5 is a schematic of three torches.

The torch device employs three torch modules and a cap as a magnet holder to generate and spread OI for sterilization application. A side-view schematic of this torch array (500) is presented in FIG. 5. As shown, a torch module (507) consists of a pair of concentric electrodes (501, 502), a ring magnet (503), a gas plenum chamber (504) hosting the ring magnet (503) and holding the electrodes (501, 502), and a tubular ceramic insulator (505) tie fit with the holding rod (506) of the central electrode (501) for positioning the central electrode and insulating the conducting rod (506) from the outer electrode frame (502).

Figure 6:
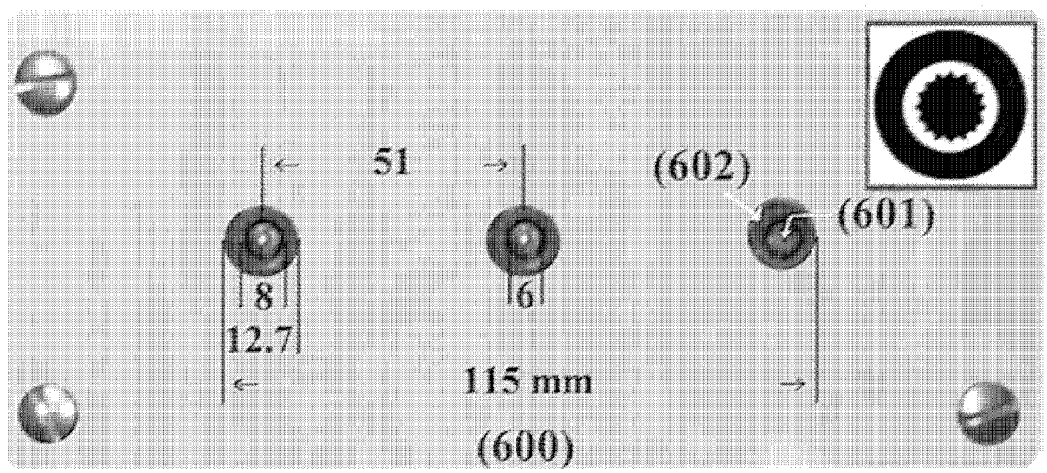
FIG. 6 is the top view of the torch array; the insert is a schematic of electrodes.

FIG. 6 is a photo of a plate (600) hosting the torch modules. It shows the shapes and dimensions of the electrodes (601, 602). The central electrode (601) is a spline copper disk with a diameter of 6 mm, i.e., the side surface of the disk is carved with grooves as shown in the insert at the upper right-hand side corner of FIG. 6. The spline structure improves the performance of the discharge and increases the airflow for a fixed gap. The central electrode is held by a conducting rod (506), which ties fit with a tubular ceramic insulator (505) used to position the central electrode and to insulate the holding rod (506) from the outer electrode frame (502). The ring-shaped outer electrode (602) has inner and outer diameters of 8 and 12.7 mm. Thus, the gap between the central and outer electrodes is 1 mm. The separation between two modules is 51 mm.

The gas plenum chamber (504) hosting a ring-shaped permanent magnet (503) (35 (od)×17.5 (id)×6.5 mm) and holding the electrodes (501, 502) has a number of holes on its side wall as the airflow inlets. Similarly, holes are also introduced on the side wall of the outer electrode frame (502) of the module.

Figure 2:
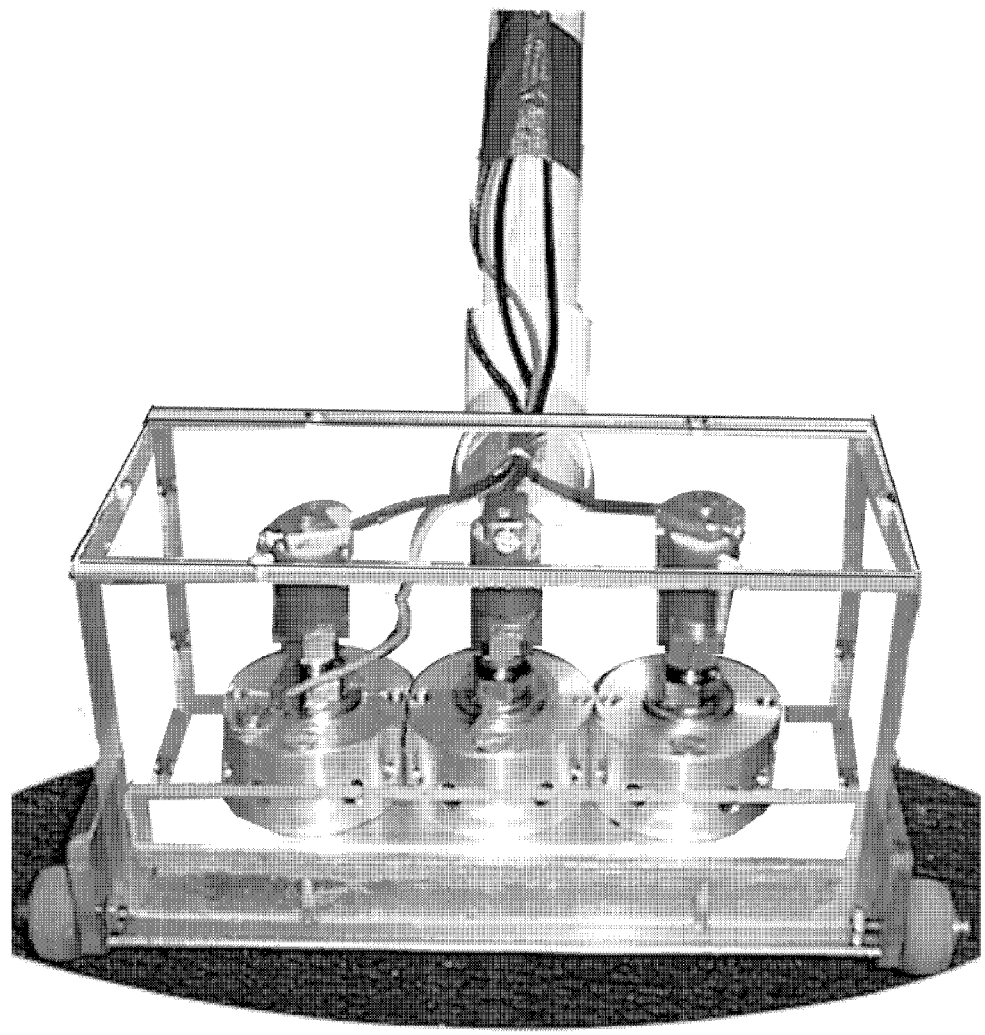
FIG. 2 is a photo of an Atomic Oxygen Generator/Sprayer.
Figure 7:
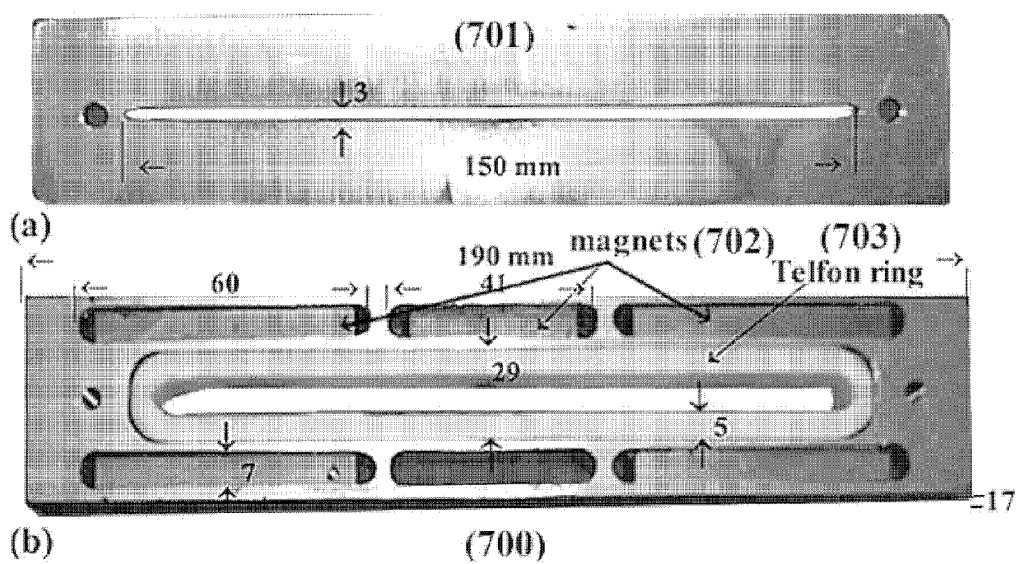
FIG. 7 shows the structure of the cap, which spreads the torches laterally.

The torches are covered by a rectangular cap (700) with a slit opening of 150×5 mm on its top cover (701), presented in FIG. 7a, as the torch exit. Three pairs of rectangular magnets (702) are held onto the two side walls of this cap (700) as shown in FIG. 7b; two pairs of permanent magnets (54×7×15 mm) are used to spread the torches at the two sides and a smaller pair (35×7×15 mm) is used for the middle torch. Also shown in FIG. 7b is a Teflon ring (703) used to shield discharges from the side walls of the cap, which helps forcing the torches to exit the slit of the cap for applications. This cap spreads torches laterally into fan-shape and also separating the hot regions of the torches from the application region. The torch modules are then contained in an air tie box that has an air inlet connected to the air pump as demonstrated in FIG. 2. In the operation, airflow delivered by the air pump passes through holes on the surfaces of gas plenum chambers (504) and outer electrode frames to the gaps between electrodes.

Figure 8:
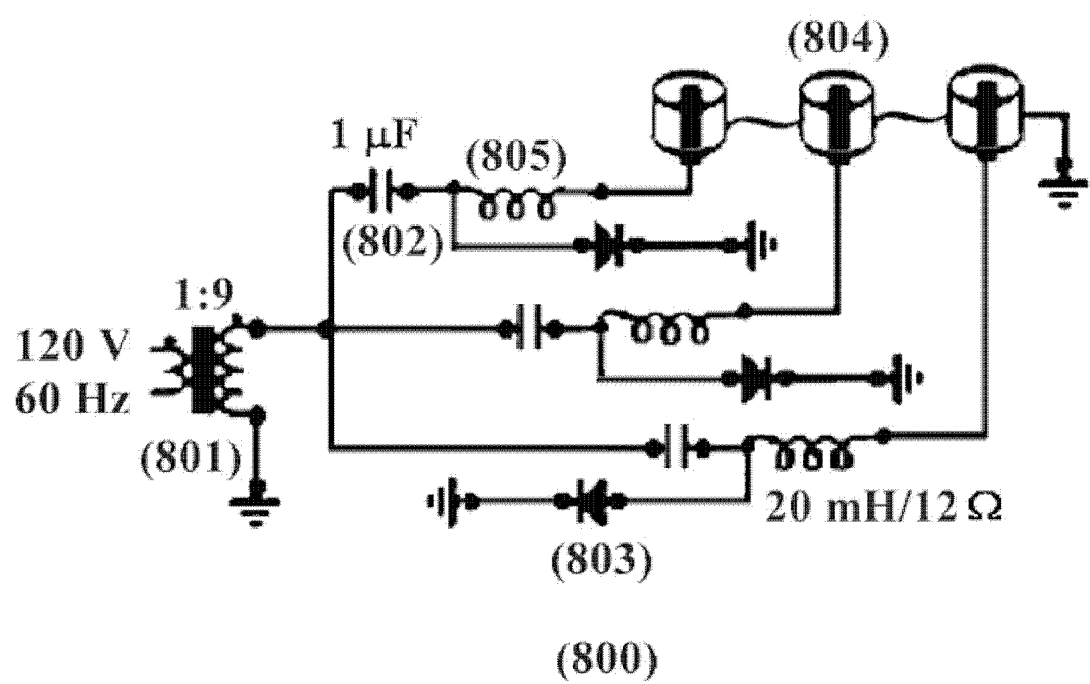
FIG. 8 is the circuitry of the power supply.

The present invention uses a power supply (800) having a circuitry shown in FIG. 8 that is simple and is adaptable to a number of AC power sources, such as 60 Hz (or 50 Hz) voltage available at most common wall outlets. This power supply employs a single power transformer (801) with a turn ratio of 1:9 to step up line voltage of 120 V (rms) to 1.08 kV (rms), i.e., a peak voltage of 1.53 kV. This peak voltage is doubled by introducing a half-wave rectifier circuit consisting of a capacitor (802) (1 μF) and a diode (803) (15 kV and 750 mA rating) as shown in FIG. 8. The capacitors also function as ballasting components, so that the discharge in one torch module (804) will not short out the voltages applied to the other modules. The inductor (805) (20 mH/12Ω) connected in series with the torch module is used to suppress the high frequency noises generated in discharges. As shown on the right hand side of FIG. 1, the power supply (103) and an air pump (104) are arranged in the same container so that the power supply (103) is cooled by the inflow to the air pump (104) that drives outflow to the torch modules (507).

§4.3 Application of the Invention

§4.3.1 Sterilization

A device made in accordance with the present invention, such as that described in §4.2, may be used as atomic oxygen generator and spray. Such a spray of dry decontaminant may be used to kill microbes in/beneath carpets, and on clothes and bed sheets.

Figure 3:
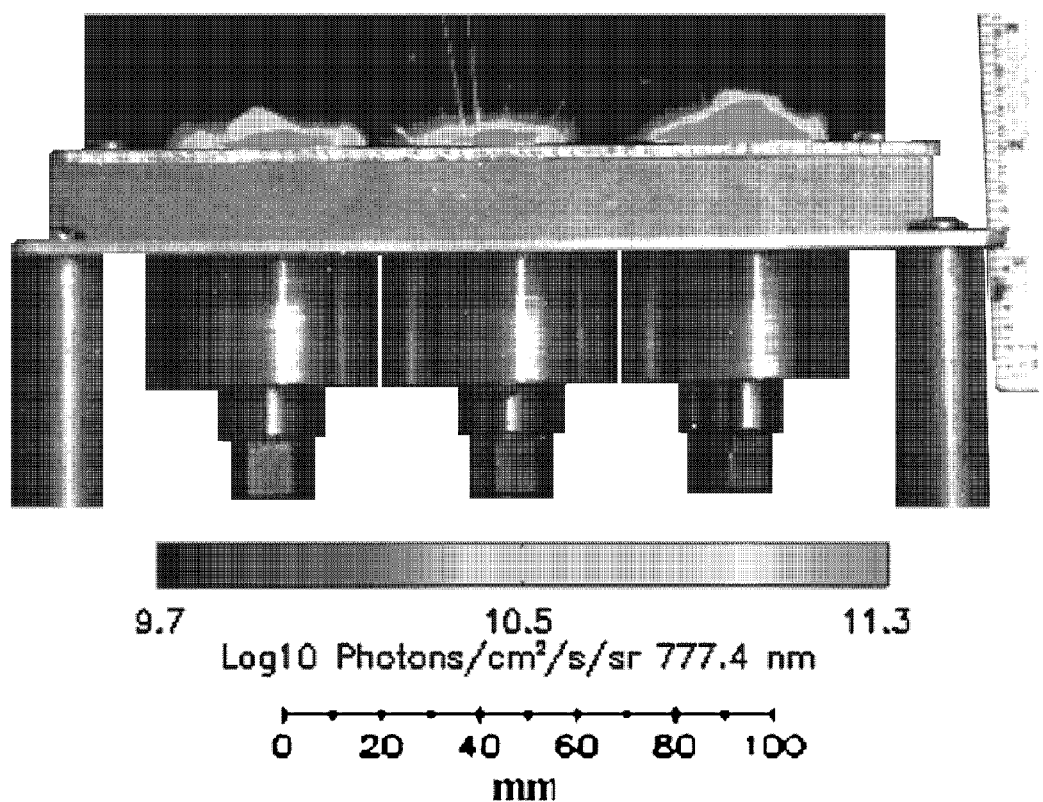
FIG. 3 is a composite image showing a triple torch setup (black and white) superimposed with false-color calibrated images of 777.4 nm emissions of spread plasma torches recorded by a narrow-band-filtered CCD camera.
Figure 4:
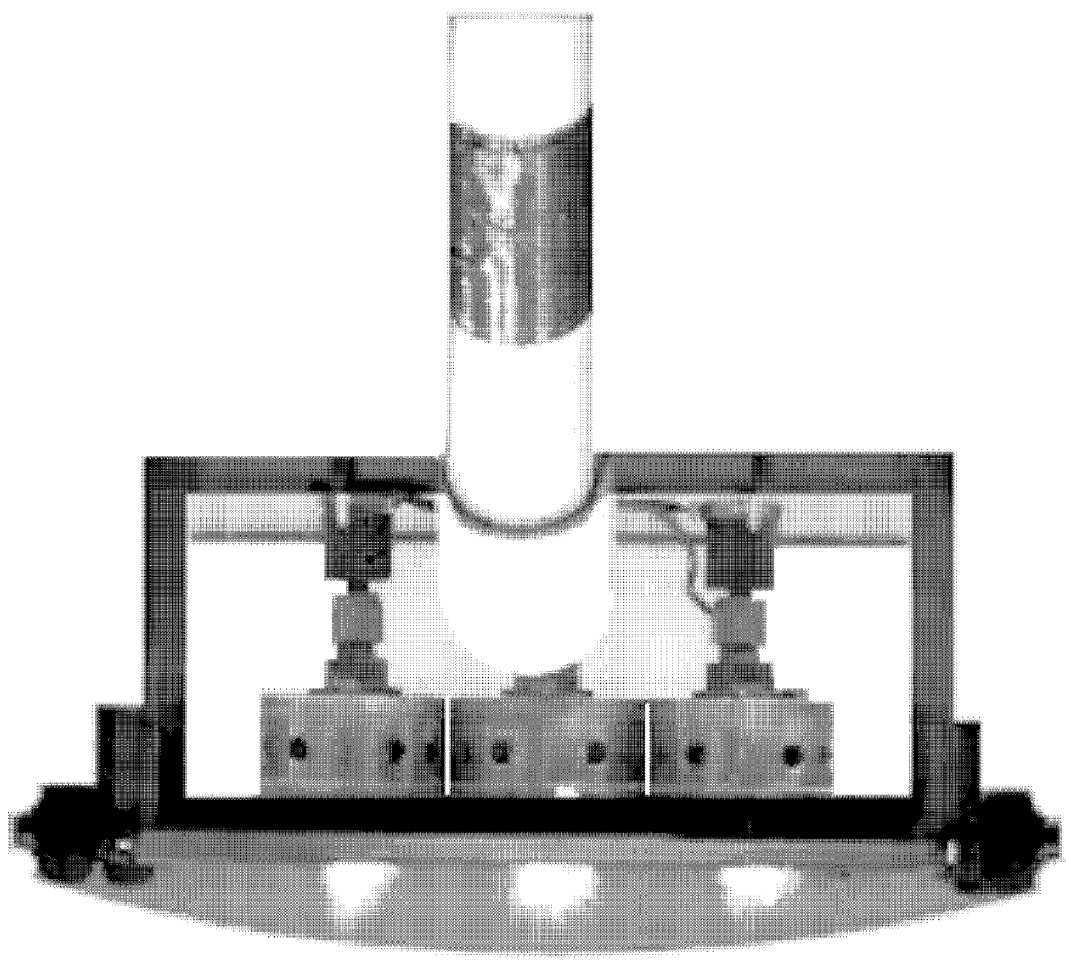
FIG. 4 is a demo the operation of the device.

The emission spectroscopy of the plasma torch generated by the embodiment of the present invention described in §4.2 was analyzed to deduce the information on the intensity and spatial distribution of atomic oxygen generated by the plasma torch. The oxygen triplet spectrum around 777.4 nm, shown in FIG. 3, verifies the generation atomic oxygen, which is the most reactive oxygen species and can destroy just about all kinds of organic contaminants by means of chemical reactions causing irreversible protein degradation and eventually, converting contaminants into carbon dioxide and water.

The device of the present invention operates with air discharge, thus no mass storage requirement in its operation. As indicated by the color bar in FIG. 3, the total photon emissions at 777.4 nm from a slice of a spread torch exceeds $10^{11}$ cm$^{-2}$ sec$^{-1}$. The density of OI is estimated to be about $4 \times 10^7$ cm$^{-3}$. Using the flow speed of 20 m/s and the OI lifetime of 0.05 ms, the flux of OI in the fan-shaped torch exceeds $2 \times 10^6$ cm$^{-2}$ sec$^{-1}$ at 1 cm away from the source region, i.e., ~2 cm away from the surface of the cap. This device is based on non-thermal and dry approach for sterilization; the flow of plasma effluent can penetrate to the bottom of carpets and does not damage carpets as well as others such as clothes and bed sheets. Moreover, the process is "green" (i.e., no hazardous chemicals are released) as well as safe to personnel (short lifetime of RAO). These are the advantageous features for sterilization applications.

§4.4 Operations of an Exemplary Embodiment

An exemplary arc plasma torch such as that described in §4.2 above, may be run at a 60 Hz periodic mode. The breakdown voltage of the arc discharge is about 3 kV and the peak arc current is less than 5 A. Because the three torches are not in phase, the peak load current is less than 8 A. A power supply with the circuitry shown in FIG. 8 may be used to run this torch device.

§4.5 Conclusions

In practical application for such as carpet sterilization, it prefers that the plasma effluent as the decontaminant spreads over a wide area. This is done by using an array of three torches and by introducing magnetic field (provided by permanent magnets) to spread each torch from a cylindrical shape to a fan shape with a width of about 35 mm. The torches are non-thermal and electron plasma has elevated energy distribution favoring to dissociate molecular oxygen into atomic oxygen in the plasma effluent. A considerable flux of RAO ($>2 \times 10^6$ cm$^{-2}$ sec$^{-1}$) is produced; its flow speed exceeds 20 m/s and it reaches out more than 20 mm. RAO can effectively kill all kind microbes. The flow speed and spatial extent of produced RAO make the invention practical for carpet sterilization application. It sterilizes the carpet as well as its underlay, where cannot be sterilized easily by the conventional methods.

Such a carpet sterilization device may be constructed from available commercial parts together with custom designed components described in §4.2.

What is claimed is:

1. A dry disinfectant spray apparatus converting ambient air to spreading gas disinfectant, said free radicals comprising:

a linear array of three faced-downward magnetized torch modules held together in a box housing;

a rectangular cap covering the array of three torch modules with a slit on the top wall for exiting the plasma effluent of the torches; the cap holding three pairs of rectangular permanent magnets on its two side walls to spread the plasma effluent of the torches along the slit of the cap;

a power supply having three high voltage (HV) output lines connected to the central electrodes of the three torch modules to energize the torches and a common ground line connected to the outer electrodes of the torches;

an air pump supplying airflow into the box housing of the torch modules, the said box housing functioning to distribute the input airflow evenly to the gas plenum chambers of the torch modules; the said airflow, delivered from a gas plenum chamber to the electric discharge gap of a torch through the openings on the frame of the torch, functioning to push gas disinfectant, said produced by the electric discharges, out of the discharge regions for applications.

2. The apparatus of claim 1, wherein each of the said magnetized torch modules includes a cylindrical frame, a central electrode, a tubular ceramic insulator, a ring-shaped permanent magnet, and a cylindrical gas plenum chamber; the said frame, inserted through a central hole on the bottom wall and held by the top wall of the gas plenum chamber to align to the central axis of the chamber, including an electrically grounded outer electrode and functioning to guide the airflow from the gas plenum chamber to the electric discharge gap of the torch; the said central electrode comprising a spline copper disk held by a conducting rod, said tie fit with a ceramic insulator to be fixed and positioned to the central axis of the frame through a connector; the said gas plenum chamber with gas inlet holes on its side wall functioning to house a ring-shaped permanent magnet, to hold the electrodes, and to feed airflow to the torch.

3. The apparatus of claim 1, wherein an inductor is connected between a high voltage (HV) output line of the said power supply and the said central electrode of a torch module; the said inductors functioning to suppress spiky current fluctuations of the discharges.

4. The apparatus of claim 1, wherein the two long sidewalls of the said cap hold three pairs of rectangular permanent magnets and are insulated from the discharges by a rectangular Teflon loop surrounding the discharge regions; the said magnetic field of the permanent magnets functioning to spread the plasma effluents of the torches laterally into a fan shape for a wide-area coverage, said extending a width exceeding 100 mm, in sterilization applications.

5. The apparatus of claim 2, wherein each of the said torch module frames has cut openings located above the bottom wall of the gas plenum chamber for passing airflow from the gas plenum chamber to the discharge gap of the torch.

6. The apparatus of claim 1, wherein each of the said plasma torches produces a plasma effluent carrying reactive oxygen as disinfectant.

* * * * *